(12) United States Patent
Umitsuki et al.

(10) Patent No.: US 6,706,492 B2
(45) Date of Patent: Mar. 16, 2004

(54) MULTIPLY TRANSFORMED KOJI MOLD AND A METHOD OF MANUFACTURING A FLAVOR ENHANCER USING THE SAME

(75) Inventors: Genryou Umitsuki, Chiba (JP); Hiroe Sato, Chiba (JP); Misao Sugishita, Chiba (JP); Yaichi Fukushima, Chiba (JP); Yasuji Koyama, Chiba (JP)

(73) Assignee: Kikkoman Corporation, Chiba (JP)

( * ) Notice: Subject to any disclaimer, the term of this patent is extended or adjusted under 35 U.S.C. 154(b) by 36 days.

(21) Appl. No.: 09/801,734

(22) Filed: Mar. 9, 2001

(65) Prior Publication Data

US 2001/0049118 A1 Dec. 6, 2001

(30) Foreign Application Priority Data

Mar. 9, 2000 (JP) ........................................ 2000-064739

(51) Int. Cl.$^7$ .................................................. C12N 1/15
(52) U.S. Cl. ........................ 435/41; 435/252.11; 426/46
(58) Field of Search .............................. 435/41, 250.11; 426/46

(56) References Cited

U.S. PATENT DOCUMENTS 5,994,113 A * 11/1999 Kauppinen et al. ......... 435/212
6,090,607 A *  7/2000 Van Den Broek et al. .. 435/223

FOREIGN PATENT DOCUMENTS

| EP | 0 427 385 A1 | 5/1991 |
| EP | 90309821.8 | * 5/1991 |
| EP | 0 967 286 A2 | 12/1999 |
| EP | 99304589.7 | * 12/1999 |
| JP | 53124693 | * 10/1978 |
| JP | 09 000164 | 1/1997 |

OTHER PUBLICATIONS

Berka, RM, et al., "The development of Aspergillus niger var. awamori as a host for the expression and secretion of heterologous gene products," *Biochem. Soc. Trans.*, vol. 19 (No. 3), 1991, pp. 681–685.
European Search Report, Jul. 10, 2001.

* cited by examiner

*Primary Examiner*—James Ketter
*Assistant Examiner*—David A. Lambertson
(74) *Attorney, Agent, or Firm*—Finnegan, Henderson, Farabow, Garrett & Dunner, L.L.P.

(57) ABSTRACT

The present invention provides a koji mold having increased protease activity and peptidase activity relative to a parent strain, a method of breeding the koji mold, and a method of manufacturing a flavor enhancer using the koji mold. More specifically, the present invention provides (1) a koji mold having increased protease activity and peptidase activity relative to a parent strain obtained by transformation using a protease gene and a peptidase gene, (2) a method of breeding the above koji mold which comprises transforming a parent strain of koji mold using a protease gene and a peptidase gene, and then selecting a transformant having higher protease activity and peptidase activity relative to a parent strain, and (3) a method of manufacturing a flavor enhancer which comprises allowing a culture product of the above koji mold to act on a protein.

7 Claims, No Drawings

SEQUENCE LISTING

<160> NUMBER OF SEQ ID NOS: 2

<210> SEQ ID NO 1
<211> LENGTH: 1593
<212> TYPE: DNA
<213> ORGANISM: Aspergillus sojae

<400> SEQUENCE: 1

```
atgaggtcgc ttttatgggc ttcgttgctt tcggggcgt tggctgggag ggcgcttgtt      60
tcgccggttc gttttttttct tcttttctttt gcgattctgg tctttttttga ttgcttttct     120 tgagcttggg tgttaagtgt tgagtgttga ctgagctaat gttatgtcta ggatgagttc     180
ccagaggata tccagttgga agatctgctg gaaggatccc aacagctcga ggactttgcc     240
tatgcctacc ccgagcgcaa tcgcgtcttt ggtggtaaag cccacgacga cacggtcaac     300
tacctctaca aggagctgaa gaagactggc tactacgatg tctacaagca gccccaggtc     360
cacctgtgga gcaatgccga ccagacgctc aaggtgggcg acgaggaaat cgaggcgaag     420
accatgacct atagtcccag cgtcgaagta actgccgatg tagccgtcgt caagaacctg     480
ggatgcagtg aggcggatta tccatccgat gtcgagggca aggtagctct catcaagcgt     540
ggagaatgtg cgttcggcga caagtcggtt ctcgctgcca aagccaaggc cgcggcttcg     600
attgtctata caaatgtggc aggatccatg gcaggcaccc ttgcgcgggc gcagagtgac     660
aagggaccgt attcggccat tgtcggtatc agcttggagg atggccagaa gctgatcaag     720
cttgctgagg ctggatcggt atctgtggat ctgtgggtgg atagcaagca ggagaaccgt     780
acgacgtata acgttatcgc gcagacgaag ggcggcgatc cgaacaatgt cgtcgcgctg     840
ggtggccaca ctgactcggt cgaggcgggc cctggtatca atgacgatgg ctcgggcatt     900
attagcaacc tggtcgttgc caaagcgctg acgcagtact ccgtcaagaa tgccgtgcgc     960
tttctcttct ggacggccga ggagttcggt ctcctgggca gcaactacta cgtctcccat    1020
```

-continued

| | |
|---|---|
| ctgaatgcca ccgagctgaa caagatcaga ctgtacctga acttcgacat gatcgcctcg | 1080 |
| cccaactacg ccctcatgat ctatgacggt gacggatcgg cgttcaacca gagcggaccg | 1140 |
| gccggatccg cccagatcga gaaactgttc gaggactact acgactccat cgacttgcct | 1200 |
| catatcccga cccagttcga cggacgttcc gattacgagg cctttatcct gaacggcatt | 1260 |
| ccggccggtg gactcttcac gggcgccgag ggcatcatgt ccgaagagaa cgcaagccgt | 1320 |
| tggggaggtc aagccggcgt ggcctacgac gccaactacc acgccgtggg agacaacatg | 1380 |
| accaacctca accatgaagc cttcctgatc aactccaaag ccacagcctt cgccgtcgcc | 1440 |
| acctacgcca acgacctatc ctcgatcccc aaacggaata ccacatcctc tctgcaccga | 1500 |
| cgagcccgca ccatgcgacc attcgggaaa agagctccga agacgcacgc tcacgtatca | 1560 |
| ggatccggat gctggcattc tcaagttgag gca | 1593 |

<210> SEQ ID NO 2
<211> LENGTH: 1209
<212> TYPE: DNA
<213> ORGANISM: Aspergillus oryzae

<400> SEQUENCE: 2

| | |
|---|---|
| atgcagtcca tcaagcgtac cttgctcctc ctcggagcta tccttcccgc ggtcctcggt | 60 |
| gcccctgtgc aggaaacccg ccgggccgct gagaagcttc ctggaaagta cattgtcaca | 120 |
| ttcaagcccg gcattgacga ggcaaagatt caggagcata ccacctgggc taccaacatt | 180 |
| caccagcgca gtctggagcg tcgtggcgcc actggcggtg atcttcctgt cggtattgag | 240 |
| cgcaactaca agatcaacaa gttcgccgcc tatgcaggct ctttcgacga tgctaccatt | 300 |
| gaggagattc gcaagaacga agatgttgcc tacgtcgagg aggaccagat ctactacctc | 360 |
| gatggcctga ctacccagaa gagtgccccc tggggtctgg gcagcatttc ccacaagggc | 420 |
| cagcagagca ccgactacat ctacgacact agtgccggcg agggcaccta tgcctacgtg | 480 |
| gtggatagcg gtgtcaatgt cgaccatgag gagttcgagg gccgcgccag caaggcctac | 540 |
| aacgctgccg gtggtcagca tgtggacagc attggccatg gcacccacgt tccggcacc | 600 |
| attgctggca agacttatgg tatcgccaag aaggccagca tcctttcggt caaagttttc | 660 |
| cagggtgaat cgagcagcac ttcgctcatt cttgacggct tcaactgggc tgccaacgac | 720 |
| attgttagca agaagcgtac cagcaaggct gcaatcaaca tgagcttggg cggtggctac | 780 |
| tctaaggctt tcaacgatgc ggtcgagaac gcattcgagc agggtgttct ctcggttgtc | 840 |
| gctgccggta acgagaactc tgatgccggc caaaccagcc ctgcctctgc ccctgatgcc | 900 |
| atcactgttg ccgctatcca gaagagcaac aaccgcgcca gtttctccaa ctttggcaag | 960 |
| gtcgttgacg tcttcgctcc cggtcaagat atcctttctg cctggattgg ctcttcctct | 1020 |
| gccaccaaca ccatctctgg tacctccatg gctactcccc acattgtcgg cctgtccctc | 1080 |
| tacctcgctg cccttgagaa cctcgatggc cccgctgccg tgaccaagcg catcaaggag | 1140 |
| ttggccacca aggacgtcgt caaggatgtt aagggcagcc taacctgct tgcctacaac | 1200 |
| ggtaacgct | 1209 |

MULTIPLY TRANSFORMED KOJI MOLD AND A METHOD OF MANUFACTURING A FLAVOR ENHANCER USING THE SAME

FIELD OF THE INVENTION

The present invention relates to a koji mold having increased protease activity and peptidase activity relative to a parent strain, a method of breeding the koji mold, and a method of manufacturing a flavor enhancer using the koji mold.

BACKGROUND OF THE INVENTION

Methods for obtaining a flavor enhancer by hydrolysis of proteins can be divided into lysis methods using microorganism culture products or enzymes (hereinafter, "enzymolysis"), and chemical lysis using acids. Examples of enzymolysis methods that have been employed include traditional methods of producing flavor enhancers such as soy sauce and miso, methods in which a koji mold culture fluid which contains protein hydrolysis related enzymes are allowed to act on proteins such as gluten.

Lysis methods using acids include high temperature processing of proteins such as gluten using hydrochloric acid.

With enzymolysis, there have been cases where the palatability of the flavor enhancer has been insufficient resulting from insufficient lysis of the protein due to the type of koji mold that is used, processing conditions, etc. In such cases increasing the amount of culture product or enzyme used may be at times effective in increasing palatability, however, this was problematic from the viewpoint of costs.

For enzymolysis, the following two enzymes can be provided as examples of enzymes greatly contributing to palatability: protease, which acts to roughly cleave and dissolve proteins; and peptidase which further breaks down amino acids from the termini of peptides (exopeptidase). Koji molds produce a plurality of proteases and peptidases, however, in the lysis of proteins, alkaline protease and a type of leucine aminopeptidase are reported to be the main actors (Nakadai: Journal of Japan Soy Sauce Research Institute 11 (2), 67–79 (1985)). For this lysis method, in order to improve of the palatability of the resultant flavor enhancer, or to reduce of amount of culture product used, there is a need to breed a koji mold exhibiting high enzyme activity. To breed koji mold, a mutation processing method has been employed. However, with methods involving mutation processing, there is the problem that great efforts are required for screening.

As a method for breeding a koji mold, a method for increasing protease activity and peptidase activity at the same time by removing inhibition of the activating ability of areA due to a nitrogen source, is the subject of a patent application (WO 99/02691). However, with this method there is the problem that a factor that controls expressions of a broad range of genes is set in an activated state.

Recently, a koji mold-derived alkaline protease gene was cloned (Japanese Patent No. 2671452; Japanese Patent No. 2888955). Further, a koji mold-derived leucine aminopeptidase gene was cloned, and by transformation with this gene, a transformant with high leucine aminopeptidase activity was obtained (Japanese Patent Laid-Open Application No. 11-346777).

However, until now, no attempt had been made to obtain a koji mold having increased activity of both enzymes by transformation using both a protease gene and a peptidase gene, and no such transformant existed.

The present invention aims to provide a koji mold having increased protease activity and peptidase activity relative to a parent strain, and a breeding method therefor. Further, the present invention aims to provide a method of producing a flavor enhancer having strong palatability.

BRIEF SUMMARY OF THE INVENTION

The present inventors, as a result of deliberate study, have succeeded in breeding a koji mold transformant having increased protease activity and peptidase activity. In the case where the culture product of this koji mold is allowed to act on a protein, when compared to the case where an equivalent amount of culture product of the parent strain is used, a higher total nitrogen concentration and total amino acid concentration, i.e. a flavor enhancer having strong palatability can be obtained. The present invention was completed on the basis of these observations.

That is, the present invention relates to the following (1)–(7):

(1) An isolated koji mold having increased protease activity and peptidase activity in relation to a parent strain resulting from transformation with a protease gene and a peptidase gene.

(2) The koji mold according to (1) above, wherein the protease gene and the peptidase gene are derived from a koji mold.

(3) The koji mold according to (1) above, wherein said koji mold is a member of *Aspergillus sojae, Aspergillus oryzae*, or *Aspergillus tamarii*.

(4) The koji mold according to (3) above, wherein the protease gene and the peptidase gene are derived from a koji mold.

(5) A method of breeding the koji mold according to any one of (1) to (4) above, comprising the steps of:

transforming a parent strain of koji mold with a protease gene and a peptidase gene; and, selecting a transformant having increased protease activity and peptidase activity relative to said parent strain.

(6) A method of manufacturing a flavor enhancer which comprises allowing a culture product of the koji mold according to any one of (1) to (4) above to act on a protein.

(7) A flavor enhancer obtainable by allowing a culture product of the koji mold according to any one of (1) to (4) above, to act on a protein.

This specification includes part or all of the contents as disclosed in the specification and/or drawings of Japanese Patent Application No.2000-64739, which is a priority document of the present application.

DETAILED DESCRIPTION OF THE INVENTION

Koji Mold of the Present Invention

The koji mold of the present invention is characterized by increased protease activity and increased peptidase activity relative to a parent strain due to transformation using a protease gene and a peptidase gene.

A "koji mold" refers to any strain which is phylogenetically a member of koji mold, and includes for example, strains used in the fermentation of food products, concretely, *Aspergillus sojae, Aspergillus oryzae, Aspergillus tamarii* and the like.

The term "protease gene" and "peptidase gene" include nucleic acid sequences which when introduced into a parent strain by transformation, can increase the activity of each enzyme of the koji mold. Such nucleic acid sequences include a structural gene of an enzyme, a mutant gene in which a mutation has been introduced within a structural gene to increase the activity of the enzyme itself, expression regulation sites (promoter, terminator, enhancer, etc.) of the structural gene, mutant expression regulation sites, expression regulation sites of different genes, or derivatives thereof, and a nucleic acid sequence consisting of a plurality of these sequences linked together. Further, the nucleic acid sequence can be of natural derivation or a synthetic product, and for example, genomic DNA, cDNA, PCR fragment, chemical synthetic/semi-synthetic DNA and the like can be used.

The derivation of structural genes for protease and peptidase is not particularly limited, and as long as they are capable of expressing in and being secreted from a koji mold, and act on a broad range of substrates, they can be derived from types of organisms other than a koji mold. From the viewpoints of intracellular production efficiency of the enzyme, efficiency of secretion to the outside of a cell, and public acceptance, it is preferable that the gene be of koji mold origin. For example, a koji mold-derived alkaline protease gene (Japanese Patent No. 2671452, Japanese Patent No. 2888955), a koji mold-derived amino peptidase gene (Japanese Patent Laid-Open Application No. 11-346777) can be used. Further, expression regulation sites of each gene can also be derived from another gene or from another type of organism if they are able to function in koji mold.

The koji mold of the present invention, to the extent that it possesses the characteristics described above, can have protease activity and peptidase activity that is increased by any factor relative to the parent strain. An example of the koji mold of the present invention where protease activity and peptidase activity is increased by a factor of at least 2 is *Aspergillus sojae* TFLAAH2 strain (FERM BP-7478) which is described more concretely in Example 1.

The Method of Breeding a Koji Mold According to the Present Invention

The koji mold of the present invention can be obtained by transforming a koji mold parent strain using a protease gene and a peptidase gene and then selecting a transformant having increased protease activity and peptidase activity relative to the parent strain.

The type of koji mold that can be used as a parent strain and the protease gene and peptidase gene are as described above. Further, to select the transformant of interest, the use of a suitable transformation marker gene is preferable with the breeding method according to the present invention.

Specific examples of a koji mold to be used as a parent strain include, *Aspergillus sojae* ATCC42251 strain, *Aspergillus oryzae* ATCC20386 strain, *Aspergillus tamarii* JCM2259 strain and the like. When actually using these strains as hosts, depending on the type of transformation marker gene to be used, a mutation is introduced where necessary for use of said marker using ordinary techniques (e.g. E. Shiela et al., Molecular and General Genetics, 218, 99–104(1989)). The transformation marker gene to be used can be appropriately chosen according to the type of parent strain or plasmid, and culture conditions or the like. For example, niaD, oliC31, pyrG, amdS, sC, argB gene or the like can be used.

The types, forms and the like of the protease gene and peptidase gene to be introduced into the parent strain are not limited, and as long as each gene in included, genes can be in the form of a PCR fragment, genomic DNA fragment, cDNA, or in the introduced state into a vector such as plasmid, in which case it is preferable that a suitable transformation marker gene is also introduced into the vector. Further, a protease gene, a peptidase gene, and where required, a marker gene, can each be situated on separate molecules, in which case the co-transformation method described below can be used.

Moreover, a gene may be either in a linear or circular form. Further, a nucleic acid sequence for improved efficiency of transformation or other genetic operations can be added before or after each gene.

Methods for transforming a koji mold are not particularly limited and include, for example, the method described in E. Shiela et al.: Molecular and General Genetics, 218 99–104 (1989). This method involves preparing protoplasts which have had cell walls removed by processing a liquid culture of koji mold by enzymolysis of the cell wall, incubating the protoplasts together with DNA in the presence of potassium chloride and polyethylene glycol 4000, and thereafter regenerating the protoplasts on a selective medium adapted for the marker gene to be used.

When performing co-transformation, a strain into which the gene of interest has been introduced and a strain into which only a selective marker has been introduced are grown on a selective medium. Here, it is necessary to perform selecting step according to activities. As a method for selecting a high activity strain, for example, by growing strains on a paper disc, the rough activity level of many test subjects can be easily measured. Specifically, when measuring an alkaline protease as a protease, and an aminopeptidase as a peptidase, measurement can be performed for example as in the below-described measurement method 1. Further, when precisely measuring each activity after selection, for alkaline protease, measurement can be performed by normal methods using milk casein as a substrate (the method according to *Soy Sauce Testing Method* published by Japan Soy Sauce Research Institute), and for aminopeptidase, measurement can be performed by the method described in Japanese Patent Laid-Open Application No. 11-346777 with leucyl-glycyl-glycine as a substrate.

In the process of transformation, a protease gene and a peptidase gene can be introduced into a parent strain simultaneously. Alternatively, transformation can be conducted in two stages. In this case, for example, a parent strain is transformed using a first gene, and a transformant having increased activity in respect of the enzyme encoded by this gene, is selected. Then this transformed strain is further transformed using a second gene, a transformant is selected which has increased activity in respect of a second enzyme.

One example of the breeding method according to the present invention is indicated in the Examples. In the Examples, first, *Aspergillus sojae* having a niaD mutation was taken as the parent strain and co-transformed with an aminopeptidase gene and niaD gene. The resultant aminopeptidase high activity transformant was co-transformed with an alkaline protease gene and oliC31 gene, thereby obtaining the koji mold of the present invention.

Measurement Method 1: A Method of Measuring Alkaline Protease Activity and Aminopeptidase Activity of a Number of Specimens 10 $\mu$l of distilled water or 0.01% (W/V) Tween-20 aqueous solution containing approximately 1000 spores (a blind study was also conducted with solution containing no spores) was applied drop-wise to a thick 8 mm $\phi$ paper disc (ADVANTEC) placed on a soy bean powder agar medium [3% (W/V) puffed defatted soy bean powder, 1% (W/V) $KH_2PO_4$, 1.5% agar powder, pH6.0], and cultured for 36 to 48 hours at 30° C. The paper disc to which mold had attached was transferred to a sample tube (INA OPTIKA, RC-0170 and the like) containing 1 ml of deionized water, and after stirring, allowed to stand for 3 or more hours at 5° C. Thereafter, activity of the supernatant as an enzyme solution was measured.

The substrate solution used in the case of protease is 1% azo-casein (Sigma) and 100 mM potassium phosphate buffer (pH7.0), and in the case of peptidase, 0.1 mmol of leucine-p-nitroanilide, dissolved in 5 ml of ethanol to which 10 ml of 500 mM Tris buffer (pH8.5) and 85 ml of distilled water is added.

In the case of protease, 50 to 100 $\mu$l of enzyme solution is placed in a sample tube (INA OPTIKA RC-0170 and the like), the protease substrate solution is added and mixed, and allowed to react for 10 to 60 minutes at 30° C. 900 $\mu$l of 10% trichloroacetic acid aqueous solution is added, vigorously mixed, and subjected to centrifugation for 10 minutes at 15,000× g. Absorption of the supernatant at 410 nm is measured, and this value minus the absorption value of the blind study material was taken as an indicator of protease activity.

In the case of peptidase, 10 to 50 $\mu$l of enzyme fluid is placed in a sample tube, 250 $\mu$l of the above peptidase substrate solution is added, mixed, and allowed to react at 30° C. for 10 to 60 minutes. 900 $\mu$l of 0.1N HCl is added and vigorously stirred, absorption at 400 nm measured, and this value minus the absorption value of the blind study material was taken as an indicator of peptidase activity.

Method for Manufacturing a Flavor Enhancer of the Present Invention

The method of manufacturing a flavor enhancer according to the present invention comprises allowing a culture product of the koji mold of the present invention to act on a protein. The method of the present invention can be applied to various flavor enhancers able to be produced using koji mold, for example, soy sauce, fish sauce, miso, animal or plant derived fermented flavorings.

The culture product of a koji mold can be a liquid culture product or a solid culture product. Further, the medium used for the culture can be of any type as long as conditions are such that would proteolysis enzyme to be produced. However, since thereafter the culture is to be used in the production of a flavor enhancer, which is a food product, a medium which is inappropriate for inclusion in a food product must not be used.

Examples of a liquid culture product include a product of an aeration-agitation culture with defatted processed soy beans, wheat bran, or soy sauce oil as a medium component. Examples of a solid culture product include soy sauce koji, miso koji, or wheat wheat bran koji obtained by ordinary methods. Culture duration differs depending on medium composition, scale of the culture, culture temperature and the like, but the culture can be performed for, for example, 12 to 96 hours, preferably 18 to 96 hours, or more preferably 36 to 72 hours. A suitable pH for the medium is between pH 4.5 and pH 9.0, and preferably between pH 5.0 and pH 8.0. A suitable culture temperature is preferably 20° C. to 40° C., and more preferably 25° C. to 35° C.

Protein to be acted on by a koji mold culture product can be any protein-containing substance, including, but not limited to, gluten (wheat, lye, oats, barley), whole soy beans, defatted processed soy beans, purified soy protein, milk casein, gelatin, fish meat, fish meat protein, livestock meat, and yeast, used alone or in combination.

As a method for allowing a culture product of a koji mold to act on a protein, the culture product can be mixed with a protein, water added as required and reacted at a suitable temperature. Culture product can typically be used as is, but an enzyme fluid obtainable by extraction of the enzyme with water or the like, or a further purified crude enzyme can also be used. Further, when the culture product per se is a composition rich in proteins such as in the case of soy sauce koji, only proteins contained in the culture product are lysed and no new protein source is required to be added.

The reaction can be performed with added NaCl and ethanol. A suitable concentration of NaCl is 20% or less, preferably, 15% or less. Ethanol concentration is 10% or less, preferably 5% or less. The entire amount of NaCl and ethanol can be added at the beginning of the reaction, but can also be added once or more in portions at suitable times during the reaction, or can be added by a continuous stream. Further, for the purposes of stabilizing color and gloss with consumption of sugars, and of preventing the growth of bacteria through the production of alcohol, yeast can be added and the reaction performed. As for the type of yeast to be used, where the NaCl concentration is low, any yeast which can be used in the production of food products such as members of Saccharomyces etc., including baker's yeast and the like can be used. Where the NaCl concentration is high, a salt-resistant yeast such as *Zygosaccharomyces rouxii* and the like is preferable.

Regarding the conditions under which a koji mold culture product is allowed to act on a protein, reactions are performed at a temperature of 4° C. to 60° C., preferably 30° C. to 55° C. and more preferably 40° C. to 50° C. Duration is typically a duration sufficient for lysis of the protein, or it can be shorter, and is preferably from 6 hours to 10 days, more preferably from 1 to 7 days.

In the case of producing a flavor enhancer which is conventionally produced by protein hydrolysis, such as soy sauce and the like, the reaction can be performed according to ordinary methods.

After the reaction is complete, solids can be removed by standard methods. Examples of methods for removing solids include filtration, centrifugation and the like.

A flavor enhancer obtained in this manner, when compared with the case where the same amount of culture product of a parent strain is used, has higher total nitrogen concentration and higher total amino acid concentration, and stronger palatability. Total nitrogen concentration and total amino acid concentration can be measured according to conventional methods.

EXAMPLES

The present invention will be explained in more detail by way of the following examples. However, these examples are not intended to limit the scope of the present invention.

Example 1

Obtaining a Koji Mold of the Present Invention

In example 1, a koji mold having increased alkaline protease activity and increased aminopeptidase activity relative to a parent strain was obtained by transformation 1. *Aspergillus sojae* (ATCC42251) strain was used as a parent strain. An aminopeptidase gene derived from *Aspergillus sojae* was used as a peptidase gene (Japanese Patent Laid-Open Application No. 11-34677). As a protease gene, a DNA sequence in which a promoter and a terminator for an *Aspergillus oryzae*-derived amylase gene and an *Aspergillus oryzae*-derived alkaline protease gene (cDNA)(Japanese Patent No. 2671452) are linked together, was used.

2. A parent niaD-mutant strain was obtained by the method of E. Shiela et al., Molecular and General Genetics, 218, 99–104(1989) Next, by co-transformation with niaD gene, the niaD-mutant strain was transformed with the aminopeptidase gene.

As the above aminopeptidase gene, DNA in which a DNA fragment comprising the nucleotide sequence set forth in SEQ ID NO.: 1 was inserted into the BamHI cleavage site of plasmid PBK-CMV, was used.

In the nucleotide sequence set forth in SEQ ID NO.: 1, the portion corresponding to nucleotide nos. 67 to 171 is an intron whereas the remaining portions are exons of an aminopeptidase structural gene.

By the above, a transformant strain TFLW22, which had, in the case where measurement was conducted with wheat bran koji, approximately 5 times greater aminopeptidase activity than the parent strain, was obtained 3. The transformant TFLW22 strain obtained above was co-transformed with pMAR5-alp1 and pMW11 according to the method of E. Sheila et al (supra). pMAR5-alp1 is a plasmid obtained by inserting a fragment comprising an *Aspergillus oryzae* alkaline protease gene (cDNA) consisting of the nucleotide sequence set forth in SEQ ID NO.: 2, into the EcoRI cleavage site of pMAR5 (Shibuya et al., Bioscience, Biotechnology, and Biochemistry 56(10), 1674–1675 (1992)) and having a structure wherein the above alkaline protease gene exists on pUC118.

pMW11 contains a marker gene. Plasmid pMW11 (Ward et al., Molecular and General Genetics 202, 265–270 (1986)) on which resides oliC31 which is an *Aspergillus nidulans* oligomycin-resistant mutant gene was cleaved at both sides of the oliC31 gene with HinDIII and PstI, and used.

After co-transformation, protoplasts were regenerated in a Czapek Dox medium (DIFCO) and transformants were selected by stratification of an oligomycin-containing Czapek Dox medium.

68 transformants are thus obtained. From the nature of co-transformation, these transformants had an oliC31 gene incorporated therein, but only some of these had an alkaline protease gene incorporated simultaneously therein. Here, when alkaline protease activity of these 68 strains of transformant was measured according to the above-described measurement method 1, it was found that activity was increased in about half of these strains. 4 strains with highest activity were selected, and isolation of individual spores was performed. The alkaline protease activity of 6 colonies for each of these strains was measured again. Then, single spore separation was further performed in respect of 3 colonies with highest activity, and the alkaline protease activity and aminopeptidase activity of 8 colonies for each of these strains, were measured.

As a result of the above, an *Aspergillus sojae* strain, TFLAAH2 was obtained which had aminopeptidase activity of approximately 5 times greater, and alkaline protease activity of approx. 3 times greater than the parent strain as measured with wheat bran koji. *Aspergillus sojae* TFLAAH2 strain was deposited at the National Institute of Bioscience and Human-Technology, National institute of Advanced Industrial Science and Technology (1–3, Higashi, 1-chome Tsukuba-shi, Ibaraki-ken, 305–8566, Japan) on Mar. 8, 2000 under Accession No. FERM P-17770. This deposition was then transferred as FERM BP-7478 to International Deposition under the Budapest Treaty on Mar. 2, 2001.

Example 2
A Method of Producing a Flavor Enhancer Using a Culture Product of the Koji Mold of the Present Invention Protein was hydrolyzed with the culture product of *Aspergillus sojae* TFLAAH2 strain of koji mold obtained in Example 1 (Test Strain) or with the culture product of parent strain *Aspergillus sojae* ATCC42251 (control strain), and a flavor enhancer produced.

Production Example 1

20 L media containing 2.5% wheat bran, 0.5% defatted soy bean, 0.1% (W/V) $KH_2PO_4$, 0.4%(v/v) soy sauce oil, were placed in two 30 L jar fermenters, and were sterilized with steam under pressure according to ordinary methods. After cooling to 30° C., the one jar fermenter was inoculated with test strain koji and the other with control strain koji (wheat bran koji prepared according to ordinary techniques), and both were cultured for 70 hours at 30° C. During this period, the culture was set such that when the pH fell below 6.8, sodium hydroxide solution was added automatically, thereby maintaining pH at or above 6.8. Aeration was at 0.5VVM, and agitation at 450 rpm.

After completion of the culture, a portion of the culture fluid was filtered, and measurement of alkaline protease activity with milk casein as a substrate, and measurement of aminopeptidase activity with leucyl-glycyl-glycine as a substrate, was performed. Results are shown in Table 1. Values in the Table 1 are relative values with the enzyme activity of the control strain taken to be 100. Compared to the control strain, the test strain exhibited approximately 3 times greater alkaline protease activity and approx. 7 times higher aminopeptidase activity.

TABLE 1

| Strain | alkaline protease activity | aminopeptidase activity |
| --- | --- | --- |
| Control Strain | 100 | 100 |
| Test Strain | 312 | 698 |

Production Example 2

Analysis was performed with the above culture fluid of the test strain and control strain. 20 ml of culture fluid, 130 g of NaCl, 300 g of wheat gluten and 800 ml of hot water (45° C.) were mixed and hydrolysis performed at 43° C. for 72 hours while subjecting the mixture to mechanical agitation using a propeller. These reaction products were filtered, and the total nitrogen concentration and total amino acid concentration of the filtrate were measured. These results, as shown in Table 2, indicated that values for total nitrogen concentration and total amino acid concentration were both higher in the test than in the control.

TABLE 2

| Strain | total nitrogen conc. (%) | Total amino acid conc. (%) |
| --- | --- | --- |
| Control Strain | 1.21 | 2.7 |
| Test Strain | 2.04 | 6.4 |

Production Example 3

To soy sauce koji obtained by a conventional method using the test strain and the control strain (pre-treatment weight of raw materials: defatted soy beans 350 g, wheat 350 g), 140 g of NaCl and 1250 ml of water were added, mixed, and hydrolysis performed at 43° C. for 60 hours while subjecting the mixture to mechanical agitation using a propeller. These reaction products were filtered and the filtrates analyzed. Results of this analysis, as shown in Table 3, indicated that values for total nitrogen concentration and total amino acid concentration were both higher in the test than in the control.

TABLE 3

| Strain | total nitrogen conc. (%) | total amino acid conc. (%) |
|---|---|---|
| Control strain | 1.07 | 2.9 |
| Test Strain | 1.51 | 3.7 |

Production Example 4

100 g of wheat bran koji obtained by conventional methods using the test strain and the control strain and 400 g of wheat gluten were added to 1300 ml of NaCl solution, mixed, and hydrolysis performed at 43° C. for 72 hours while subjecting the mixture to mechanical agitation using a propeller. These reaction products were filtered. Analysis of the filtrate, as shown in Table 4, indicated that values for total nitrogen concentration and total amino acid concentration were both higher in the test than in the control.

TABLE 4

| Strain | total nitrogen conc. (%) | total amino acid conc. (%) |
|---|---|---|
| Control Strain | 2.12 | 2.4 |
| Test Strain | 2.94 | 3.3 |

It was indicated that in any production examples, by using a culture product of the koji mold of the present invention, a flavor enhancer exhibiting higher palatability can be produced than by using the parent strain.

By the present invention, there is provided a koji mold having increased protease activity and peptidase activity relative to a parent strain, and a method for breeding the same. Further, by allowing a culture product of the koji mold of the present invention to act on a protein, it was possible to obtain a flavor enhancer having stronger palatability than that which can be obtained using the parent strain. The present invention is thus extremely useful to industry.

All publications, patents and patent applications cited herein are incorporated herein by reference in their entirety.

What is claimed is:

1. An isolated koji mold having increased protease activity and peptidase activity in relation to a parent strain, wherein the isolated koji mold results from transformation with a protease nucleic acid sequence and a peptidase nucleic acid sequence, and wherein the isolated koji mold has at least 3 times greater protease activity and at least 5 times greater peptidase activity than the parent strain.

2. The isolated koji mold according to claim 1, wherein the protease nucleic acid sequence and the peptidase nucleic acid sequence are of koji mold origin.

3. The isolated koji mold according to claim 1, wherein said isolated koji mold is a member of *Aspergillus sojae, Aspergillus oryzae,* or *Aspergillus tamarii.*

4. The isolated koji mold according to claim 3, wherein the protease nucleic acid sequence and the peptidase nucleic acid sequence are of koji mold origin.

5. A method of obtaining the isolated koji mold according to any one of claims 1 to 4 comprising the steps of:

(a) transforming a parent strain of koji mold with a protease nucleic acid sequence and a peptidase nucleic acid sequence; and, (b) selecting a transformant having increased protease activity and peptidase activity relative to said parent strain.

6. A method of manufacturing a flavor enhancer which comprises allowing a culture product of the isolated koji mold according to any one of claims 1 to 4 to act on a protein, thereby manufacturing a flavor enhancer.

7. An isolated koji mold having increased protease activity and peptidase activity in relation to a parent strain, wherein the isolated koji mold results from transformation with a protease nucleic acid sequence and a peptidase nucleic acid sequence, and wherein the protease nucleic acid sequence encodes the same amino acid sequence as that encoded by the nucleotide sequence of SEQ ID NO:2, and the peptidase nucleic acid sequence encodes the same amino acid sequence as that encoded by the nucleotide sequence of SEQ ID NO: 1.

* * * * *